(12) United States Patent
Schlatterer (10) Patent No.: US 11,617,674 B2
(45) Date of Patent: Apr. 4, 2023

(54) SYNDESMOSIS REDUCTION DEVICE AND METHOD OF USE

(71) Applicant: Daniel Robert Schlatterer, Dunwoody, GA (US)

(72) Inventor: Daniel Robert Schlatterer, Dunwoody, GA (US)

( * ) Notice: Subject to any disclaimer, the term of this patent is extended or adjusted under 35 U.S.C. 154(b) by 519 days.

(21) Appl. No.: 15/792,976

(22) Filed: Oct. 25, 2017

(65) Prior Publication Data

US 2019/0117436 A1    Apr. 25, 2019

(51) Int. Cl.
*A61F 13/00* (2006.01)
*A61F 5/058* (2006.01)
*A61F 13/06* (2006.01)
*A61F 13/02* (2006.01)

(52) U.S. Cl.
CPC ............ *A61F 5/0585* (2013.01); *A61F 13/00* (2013.01); *A61F 13/00004* (2013.01); *A61F 13/00038* (2013.01); *A61F 13/0273* (2013.01); *A61F 13/066* (2013.01)

(58) Field of Classification Search
CPC ...... A61F 13/066; A61F 13/064; A61F 13/06; A61F 13/00; A61F 13/00004; A61F 13/00038; A61F 5/0111; A61F 13/0273; A61F 13/0269; A61F 13/10; A61F 13/08; A61F 13/085; A61F 5/0585; A61F 5/0113; A61F 13/102; A61F 13/062; A61F 13/108; A61F 5/04; A61F 5/058; A61F 5/05; A61F 5/01; A61F 13/146; A61F 13/148; A61F 13/14; A61F 13/145; A61F 13/143; A61M 25/02; A63B 21/0552; A63B 21/0555
USPC ................... 602/75, 76, 77; 2/338; 128/876
See application file for complete search history.

(56) References Cited

U.S. PATENT DOCUMENTS

| 2,744,252 | A | * | 5/1956 | Cansler | A45D 44/08 |
| | | | | | 2/50 |
| 3,736,596 | A | * | 6/1973 | Milne | A41D 1/00 |
| | | | | | 2/74 |
| 4,215,687 | A | * | 8/1980 | Shaw | A61F 13/06 |
| | | | | | 128/DIG. 15 |
| 5,662,599 | A | * | 9/1997 | Reich | A61F 13/0269 |
| | | | | | 602/59 |
| 6,257,240 | B1 | | 7/2001 | Shesol | |
| 6,258,051 | B1 | | 7/2001 | Shesol et al. | |
| 6,506,175 | B1 | * | 1/2003 | Goldstein | A61F 13/06 |
| | | | | | 602/60 |

(Continued)

FOREIGN PATENT DOCUMENTS

| CN | 205832014 | 12/2016 |
| CN | 206081217 | 4/2017 |

*Primary Examiner* — Victoria Hicks Fisher
(74) *Attorney, Agent, or Firm* — David L. King (57) ABSTRACT

An improved syndesmosis reduction device has a wrap of elastic material extending a length L from a first end to a second end with an open window or slot positioned in an intermediate portion of the wrap spaced from the ends. The wrap causes a reduction of an injured ankle and is facilitated by the elastic nature of the wrap. The reduction is facilitated by circumferentially wrapping the wrap from a leg to a foot or vice versa in a compressive fashion by securing the first end by wrapping and stretching the wrap to the second end. The window or slot is to permit an incision at the ankle for hardware placement without the need to remove the wrap and without loss of the reduction achieved.

8 Claims, 10 Drawing Sheets

(56) References Cited

U.S. PATENT DOCUMENTS

| | | | |
|---|---|---|---|
| 6,617,485 B2 * | 9/2003 | Herzberg | A61F 5/0111 602/23 |
| 8,535,256 B2 * | 9/2013 | Taylor | A61F 13/06 602/75 |
| 2014/0259263 A1 * | 9/2014 | Khapchik | A41D 27/00 2/67 |
| 2015/0045710 A1 | 2/2015 | Pastor | |

* cited by examiner

PRIOR ART

PRIOR ART

SYNDESMOSIS REDUCTION DEVICE AND METHOD OF USE

TECHNICAL FIELD

The present invention relates to an improved, faster, safer and more effective method of reducing a syndesmotic injury.

BACKGROUND OF THE INVENTION

Ankle injuries can be either bony injuries including fractures, or they may be a purely ligamentous injury, or a combination of both. On the outside of the ankle on the lateral side is an articulation between the distal fibula and the distal Tibia. The distal lateral tibia contains a concavity or incisura in which the distal fibula sits. The distal fibula is held in place by a series of ligaments. If these ligaments are torn through athletic competition or other traumatic events the fibula moves from its resting position. This can create a painful and unstable ankle joint, not suitable for walking, or running.

Returning the fibula to its anatomic position is followed by placement of a holding screw in a surgical procedure until the ligaments heal. The reduction of this distance between the distal lateral tibia and the distal fibula back to normal is essential for proper ligament repair. Often bone fractures are reduced surgically and the fracture fragments are immobilized by a metal plate which spans the fracture and has screws going through the plate into bone on either side to secure the fracture fragments while also securing reduction of the syndesmosis at a malreduction rate of nearly 50%. A large metal clamp is typically used as a reduction tool. This clamp spans the ankle and is squeezed to push the fibula back into its tibial concavity.

Studies have shown that if the clamp force vector is off by as little as 15 degrees then the fibula malreduces. Any malpositioning of the fibula results in long term ankle problems. In the present invention described hereinafter, it is proposed that an ankle wrap device be provided to achieve a more perfect syndesmosis reduction than can otherwise be obtained.

SUMMARY OF THE INVENTION

An improved syndesmosis reduction device has a wrap of elastic material extending a length L from a first end to a second end with an open window or slot positioned in an intermediate portion of the wrap spaced from the ends. The wrap is configured to achieve a reduction of an injured ankle and is facilitated by the elastic nature of the ankle wrap. The reduction is facilitated by circumferentially wrapping the wrap from a leg to a foot or vice versa in a compressive fashion by securing the first end by wrapping and stretching the wrap to the second end in the absence of clamps or secondary clamping.

The wrap may be made of any elastic rubber like material, including polymers of similar properties, elastic woven fabrics, or other stretchable materials. The ankle wrap can be made from any and all materials for elastic wrap types of devices for circumferential injury reduction to impart a uniform reduction vector resulting in an anatomic reduction until definitive fixation is applied for all other indications for circumferential wrapping, or binding, this includes use of a synthetic dressing, or any variation in material and/or variation in physical configuration thereof including but not limited to latex free, or other less allogenic materials. The wrap may be utilized for other extremity fractures or dislocations to reduce the injury.

The wrap maintains a reduction moment on the syndesmotic injury of the syndesmosis or other injury until the injury is stabilized surgically with internal hardware. The wrap is configured for external use only, is single use and disposable by standard hazardous waste laws and regulations.

A method of reducing a syndesmotic injury comprising the steps of: surgical site preparation and draping of the involved ankle; wrapping the involved leg, ankle, and foot with a wrap having an intermediate portion with an open window or slot positioned at the discretion of the surgeon but intended to be over the distal fibula to facilitate internal hardware placement without the need for removal of the wrap; proceeding with internal fixation as indicated by making an incision through the window or slot in the ankle wrap device; and once stabilized with internal fixation, the wrap is unwrapped, removed, and discarded according to manufacturer recommendations. The method of reducing a syndesmotic injury occurs by wrapping the wrap to better direct reduction vector forces on the fibula without a clamp which has two points of bony contact. The method of reducing a syndesmotic injury allows stabilizing and fixing posterior wall acetabular fracture fragments directly to dimensions of a single plate to buttress an area of fracture in combination with the wrap. The method of reducing a syndesmotic injury allows wrapping faster to achieve a more perfect reduction compared to a clamp technique and securing with hardware at the surgeon's discretion with a plate, screws, suture or other material to stabilize a fracture by utilizing the window or slot and wrapping the ankle with the wrap, the wrap can stay in place without harm to the patient, allowing the surgeon to proceed with the procedure independently with minimal to no need for assistance from additional qualified surgical assistants. The method allows for holding the reduction without the need for a secondary clamping step, maintaining the wrap in place while hardware is placed.

Definitions

As used herein and in the claims:

A syndesmosis is defined as a fibrous joint in which two adjacent bones are linked by a strong membrane or ligaments. This definition also applies for the distal tibiofibular syndesmosis, which is a syndesmotic joint formed by two bones and four ligaments. The distal tibia and fibula form the osseous part of the syndesmosis and are linked by the distal anterior tibiofibular ligament, the distal posterior tibiofibular ligament, the transverse ligament and the interosseous ligament. Although the syndesmosis is a joint, in the literature the term syndesmotic injury is used to describe injury of the syndesmotic ligaments. In an estimated 1-11% of all ankle sprains, injury of the distal tibiofibular syndesmosis occurs.

Elastic support or compression bandages: support bandages can be made of cotton fabric which covers the elastic threads. While some bandages are still manufactured with latex, many woven and knitted elastic bandages provide adequate compression without the use of natural rubber or latex. The modern elastic bandage is constructed from cotton, polyester and latex-free elastic yarns. By varying the ratio of cotton, polyester, and the elastic yarns within a bandage, manufacturers are able to offer various grades of compression and durability in their wraps.

DETAILED DESCRIPTION OF THE INVENTION

An improved syndesmosis reduction device 20 is an elastic material that has contraction properties upon being stretched. The device 20 can be made of any number of stretchable fabric options such as elastic woven fabrics, as will be explained hereinafter with reference to FIGS. 1A-11.

Figure 11:
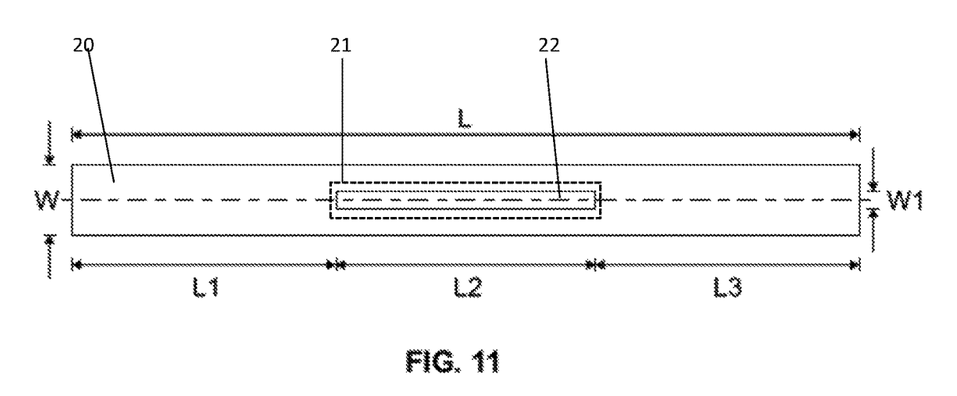
FIG. 11 is the present invention wrap with a reinforced window.

The wrap 20 of the present invention, as shown in FIG. 11, has a width of at least 8 inches wide and a length of 7 to 10 feet, preferably 9 feet in length. Often the orthopaedic surgeon desires to make a 2-4 inch incision over the distal fibula 4 laterally for hardware placement. In order to facilitate an incision and plate and screw placement, the ankle wrap device 20 will have an open window or slot 22 in an intermediate location spaced from the ends, so that as the ankle 10 is wrapped with the device 20, direct access to the fibula 4 through the open window or slot 22 makes it possible to cut an incision without having to cut the wrap device 20. This window 22 can be in a variety of dimensions and positions along the length of the ankle wrap device 20 with the end point being access to the ankle 10 for the purposes of making an incision and hardware placement. Narrow elastic bandages are commercially available, but the difference is that with the present invention device 20, a window 22 is incorporated along at least 2-4 feet of the wrap 20 for skin incision 12 and hardware placement. The inventive wrap 20 is wider and longer than any current elastic bandage and is only reinforced 21 thicker around the perimeter of the window or slit 22 to limit breakage of the wrap 20 along the window segment 22. Off the shelf, commercial elastic bandages tear in half after cutting out a window for skin access as just described. The present wrap allows for multiple modifications to be made available in the present invention elastic wrap. Currently, elastic wraps are used to exsanguinate a limb before inflation of a tourniquet. This new and improved elastic wrap would facilitate anatomic syndesmosis reduction without the need for an ankle clamp device 100 while providing an access portal for surgical incisions and hardware implantation, if desired.

Ankle injuries encompass fractures at the ankle or disruption of the ligamentous complex between the distal fibula 4 and tibia 2. This is also known as syndesmotic injuries. When the ligaments rupture, the fibula 4 subluxes or even dislocates from the distal tibia 2. Restoration of this bony relationship is technically challenging and historically has been performed by squeezing a clamp 100 between the two bones. Sometimes this results in the fibula 4 settling perfectly into the tibial concavity 3. Other times the fibula 4 is malreduced which alters the normal mechanics of the ankle joint. Research has shown that malpositioning of the clamp 100 leads to a malreduction. The purpose of this ankle wrap device 20 is to provide a more even reduction vector. Cadaver studies have demonstrated proof of this concept. In order to make this ankle wrap 20 suitable for surgical ankle procedures, a window 22 would be fashioned in the last 3 feet or so of the length of the wrap 20. This permits access to the skin for incision purposes, and hardware placement. The ankle wrap 20 is an improved method of syndesmosis reduction. This elastic wrap method may find application in other extremity fractures.

Figure 1A:
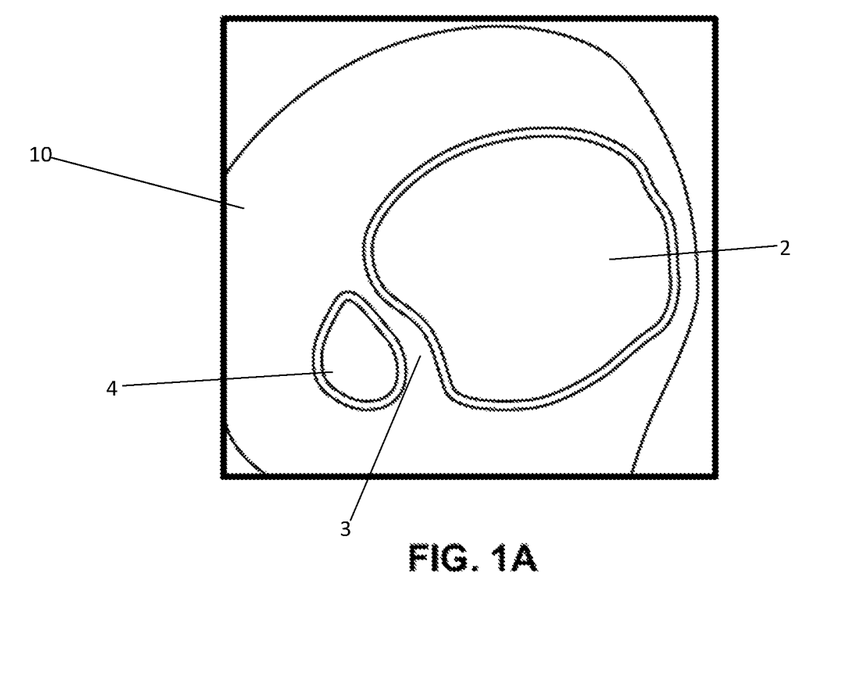
FIG. 1A is a CT scan of an exemplary first ankle with a nearly flat concavity.
Figure 1B:
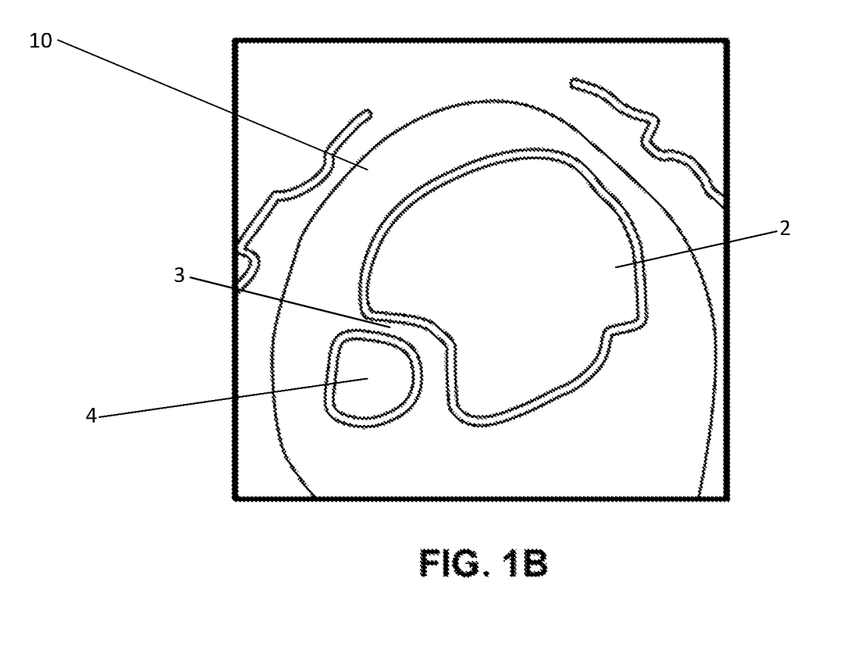
FIG. 1B is another CT scan of an ankle with a deeper concavity.

FIGS. 1A and 1B show axial CT scans of two different ankles 10 demonstrating the variability of the concavity 3 of the tibia 2 from nearly flat in FIG. 1A, to deep enough to fit the fibula 4 in FIG. 1B.

Figure 2:
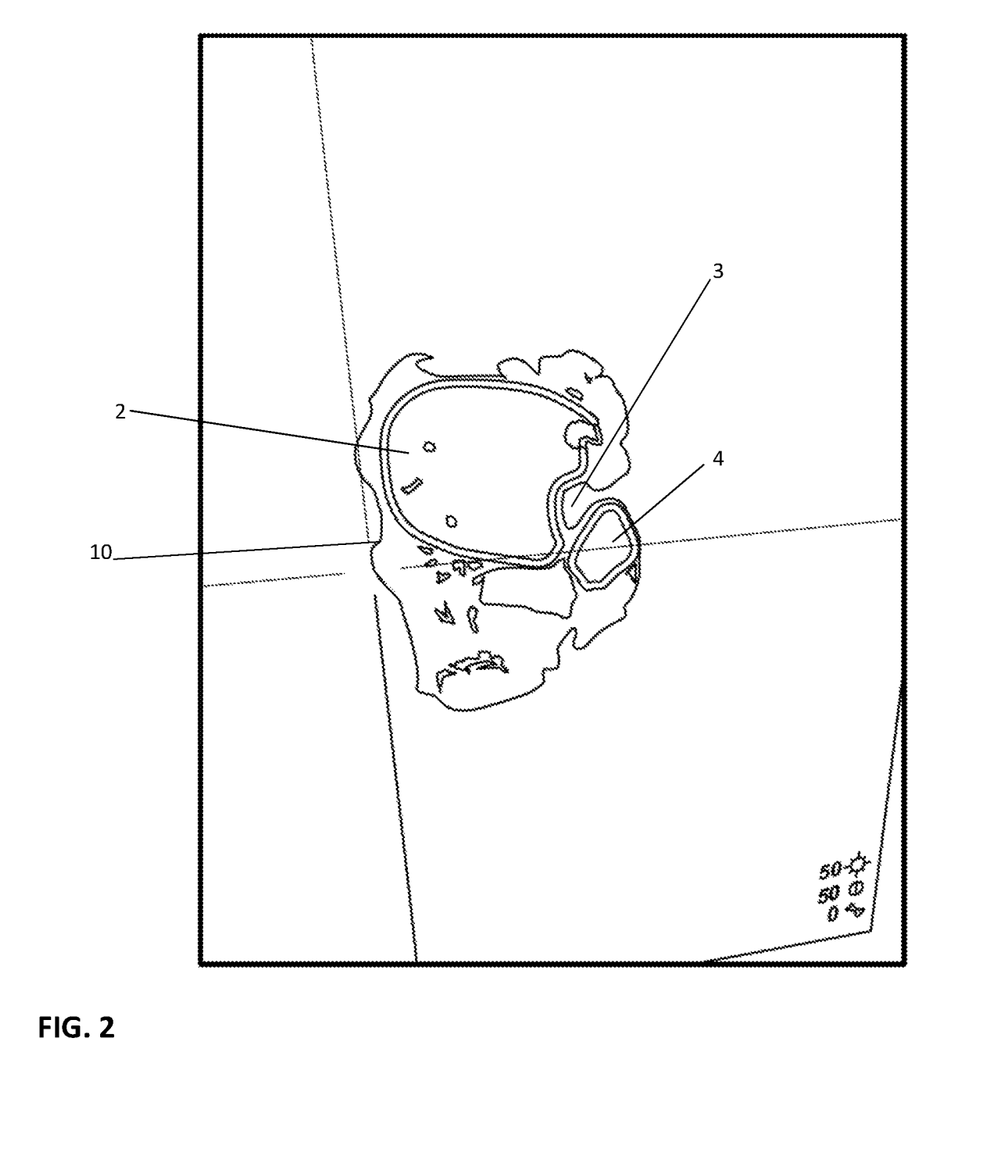
FIG. 2 is a reconstruction of a CT scan of an injured ankle.

FIG. 2 shows a reconstruction of a CT scan of a patient after sectioning all of the syndesmotic ligaments showing how the fibula 4 is no longer resting next to the tibia 2 as in FIGS. 1A, 1B. The fibula 4 has fallen down which in anatomic terms is posteriorly dislocated.

Figure 3:
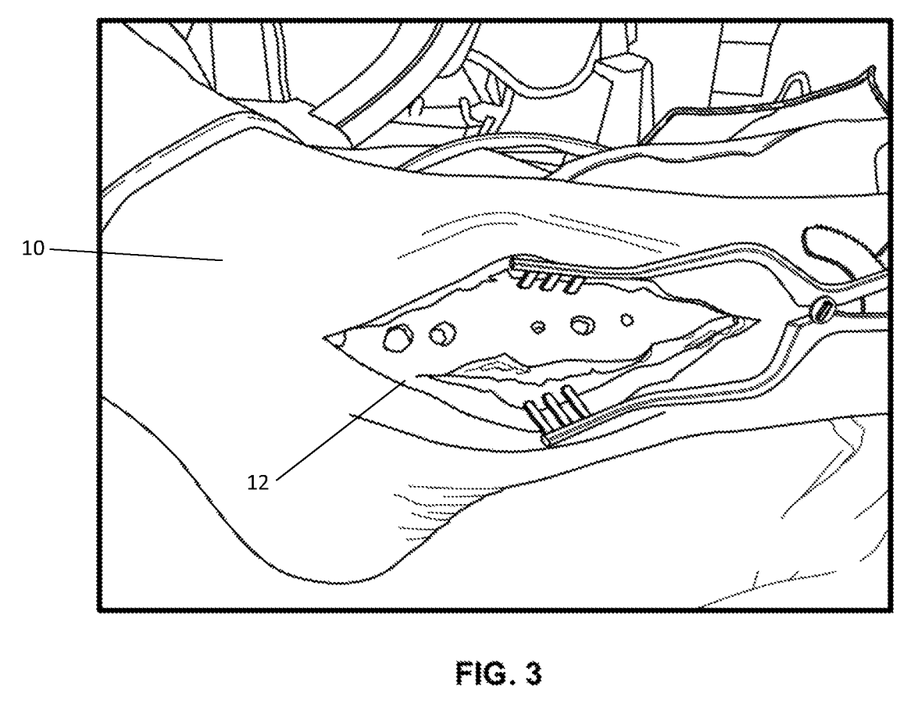
FIG. 3 is a perspective view of an example of an ankle after an incision.

FIG. 3 shows an ankle 10 after an incision to remove failed hardware. The purpose of this image is to illustrate the skin access 12 sometimes needed when treating ankle injuries. The proposed ankle wrap device would have a 2-4 inch wide seamed or reinforced window to permit this skin access 12. Current elastic wraps do not have this modification and often tear when cut to provide access.

Figure 4:
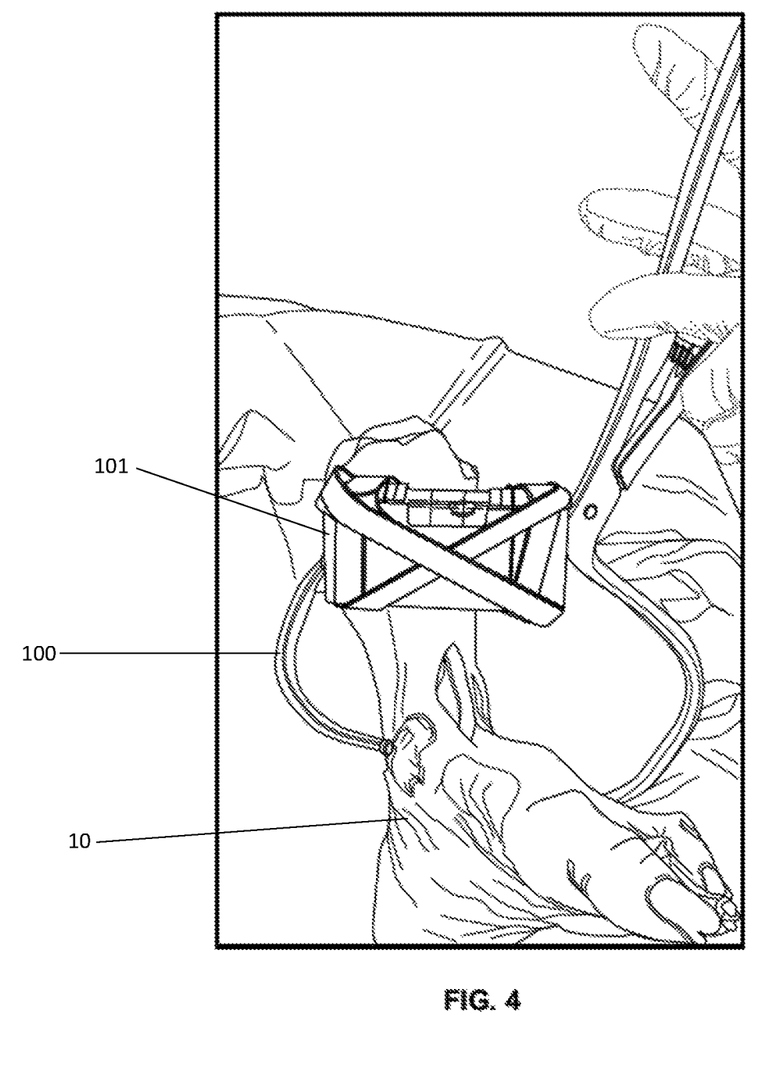
FIG. 4 is a perspective view of an exemplary cadaver ankle with the standard ankle clamp for reduction maneuvers for a disrupted syndesmosis.

FIG. 4 shows a cadaver ankle 10 used for testing the ankle wrap device, the metal ankle reduction clamp 100 is shown with the 2 points of the clamp that can be placed nearly anywhere on the lateral or fibular side and likewise nearly anywhere along the big toe or medial side of the ankle 10. The level 101 is a rectangular device with the air bubble at the top middle that was taped to the metal reduction clamp 100 to test a related reduction concept. This picture only illustrates the wide variability in clamp 100 placement, and why it is common to malreduce the syndesmosis.

Figure 5:
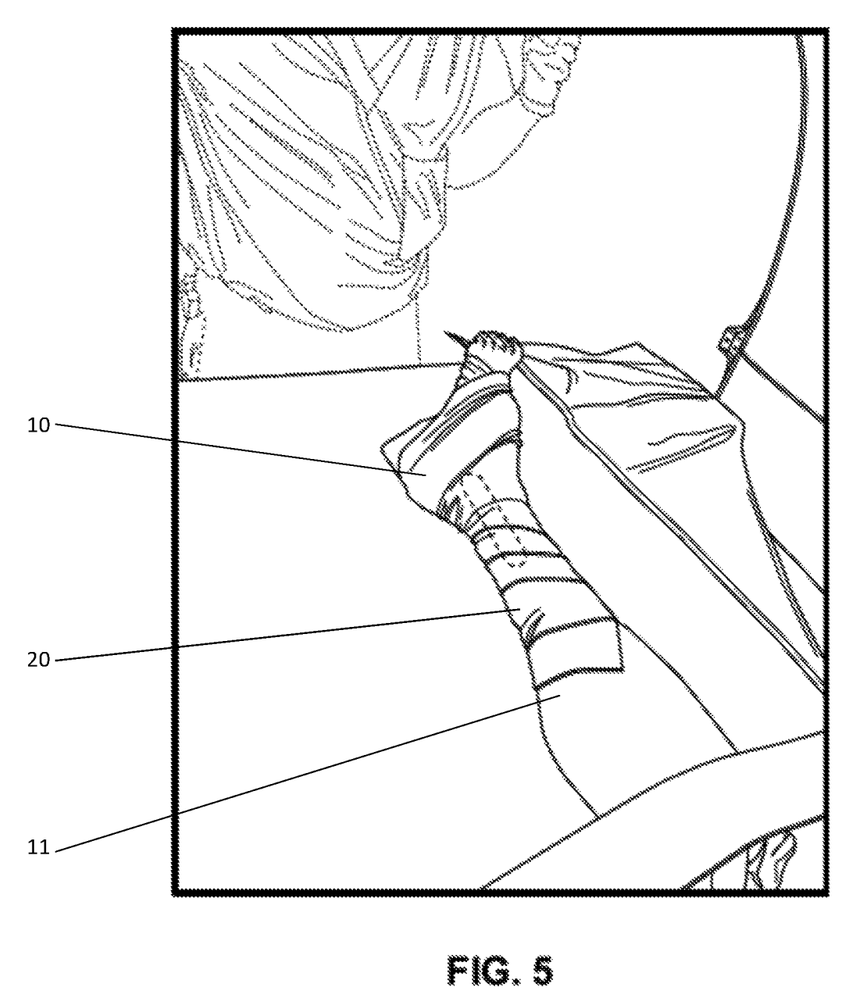
FIG. 5 shows the ankle wrap on the exemplary cadaver ankle.

FIG. 5 shows a cadaver ankle 10 used for testing the ankle wrap device 20. The ankle wrap 20 was placed starting at the lower calf 11 and wrapped until it passed the ankle 10 and onto the mid foot. The ends are shown secured under the wrap, held in place without secondary clamps or fasteners.

Figure 6:
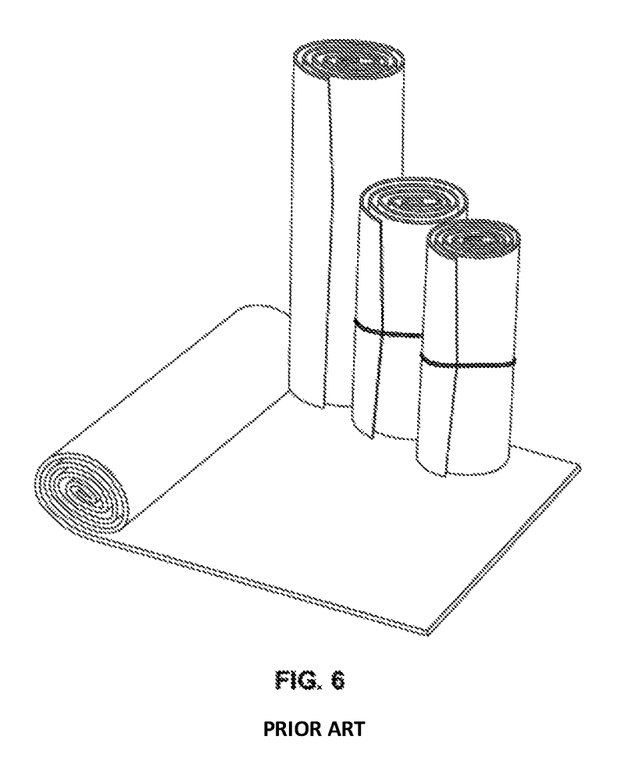
FIG. 6 is a view of prior art commercially available elastic wraps of different widths.

FIG. 6 shows 3 different widths of commercially available elastic wraps used for limb exsanguination, 4, 5 and 6 inches typically.

Figure 7:
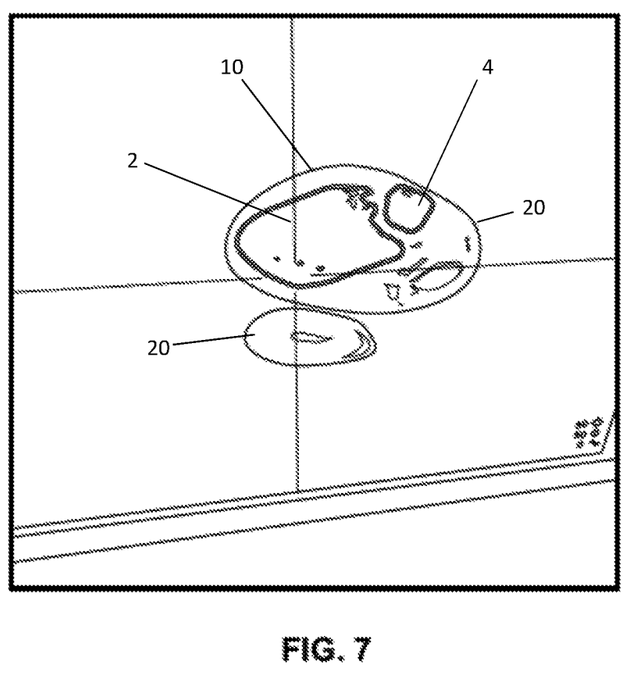
FIG. 7 is an image of the ankle wrap used to repair an ankle.

FIG. 7 shows a 3-dimensional reconstruction image after the ankle wrap 20 was used to reduce a dislocated fibula 4 which is the same as the syndesmotic injury depicted in FIG. 2. Note also some of the elastic wrap 20 still rolled up and under the ankle 10. The fibula 4 is now fully reduced and sitting anatomically next to the tibia 2.

Figure 8:
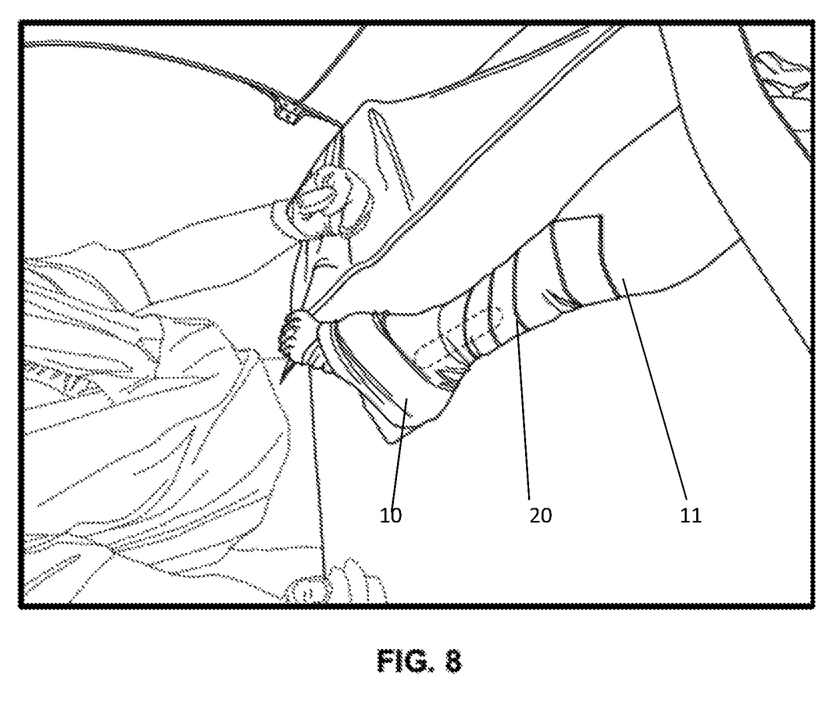
FIG. 8 is a perspective view of the ankle wrap.

FIG. 8 shows a cadaver ankle 10 used for testing the ankle wrap device 20 identical to FIG. 5. The elongated circle marking on the elastic wrap 20 marks the preferred position of a window for surgical access to the skin for hardware placement.

Figure 9:
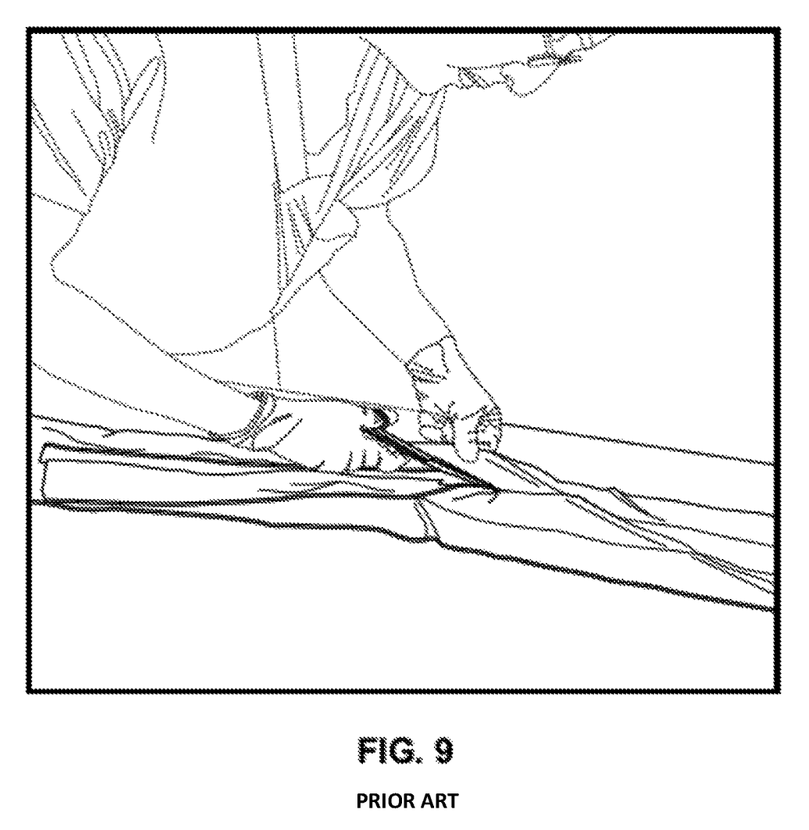
FIG. 9 shows a wrap being modified to make a window.

FIG. 9 shows a commercially available elastic being modified in order to create the window. The wrap was unrolled and a central section was cut out with scissors.

Figure 10:
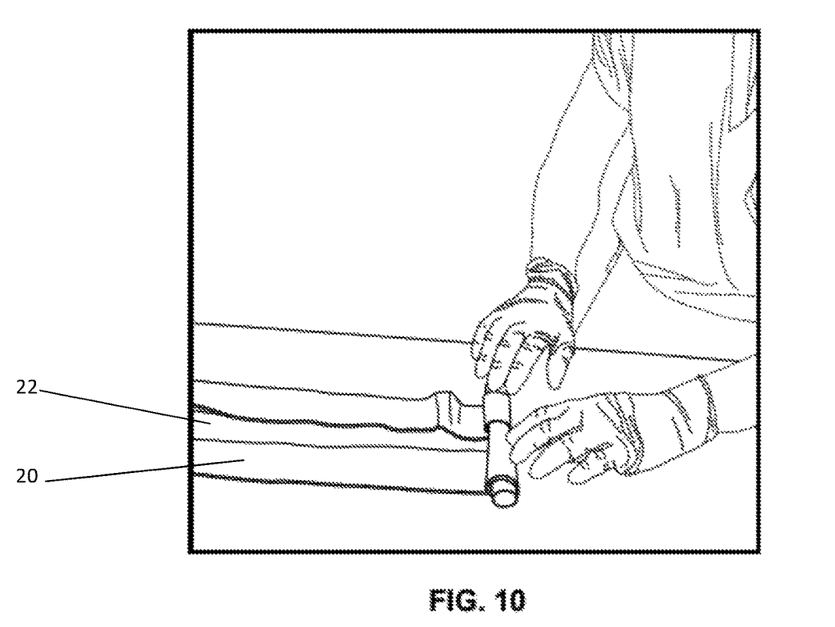
FIG. 10 is a view showing a surgeon rolling the modified wrap of the present invention.

FIG. 10 shows similar image as FIG. 9 illustrating rolling the wrap 20 back up after cutting out a central window 22 to resume testing of the wrap's ability to reduce the syndesmosis.

FIG. 11 is a view of the rectangular shaped wrap 20 of the present invention unrolled showing the various lengths and the reinforced 21 window 22 with a width W1 centered on the wrap width W; and the Length L including L1, L2 and L3. L1 being 2-4 feet long, L2 being 2-4 feet long and L3 being 2-4 feet long; preferably each being 3, 3 and 3 feet respectively with a width W at least 8 inches preferably 9 inches and a window width W1 of two inches, the window being the only reinforced portion of the wrap as shown.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. The surgical access window described herein encompasses the dimensions presented and any and all variations applicable to the methods and surgical technique described directly or indirectly intended with this device.

What is claimed is:

1. An improved syndesmosis reduction device consisting of:
a wrap of elastic material in a rectangular shape extending a length L of 7 feet to 10 feet from a first end to a second end with a width W of 9 inches, the wrap having a 2 to 4 inch wide seamed or reinforced window or slot having a length of 2 to 4 feet and a width positioned in an intermediate portion of the wrap spaced from the first and the second ends, the open window or slot being reinforced thicker around a perimeter of the window relative to the wrap, and wherein the wrap is configured to be used to reduce a syndesmotic injury by wrapping the wrap to better direct reduction vector forces on a fibula without a clamp, wherein the wrap is configured to allow a reduction to be facilitated when using the wrap by circumferentially wrapping the wrap from a leg to a foot or vice versa in a compressive fashion by securing the first end by wrapping and stretching the wrap to the second end in the absence of clamps and wherein the wrap is made of any elastic rubber or elastic polymers, elastic woven fabrics, or other stretchable materials and only reinforced along the perimeter of the window.

2. The improved syndesmosis reduction of claim 1 wherein the wrap is configured to achieve a reduction of an injured ankle and is facilitated by the elastic nature.

3. The improved syndesmosis reduction of claim 1 wherein the wrap is configured to be utilized for extremity fractures or dislocations to reduce an injury.

4. The improved syndesmosis reduction of claim 1 wherein the wrap is configured to be used by maintaining a reduction moment on a syndesmotic injury of a syndesmosis or other injury until the syndesmosis or other injury is stabilized surgically with internal hardware.

5. The improved syndesmosis reduction of claim 2 wherein the wrap is made from elastic materials for circumferential injury reduction allowing the wrap to be used to impart a uniform reduction vector resulting in an anatomic reduction until definitive fixation is applied.

6. The improved syndesmosis reduction of claim 1 wherein the wrap is configured for external use only, is single use and disposable by standard hazardous waste laws and regulations.

7. The improved syndesmosis reduction of claim 6 wherein the wrap has a fabric made with braids.

8. An improved syndesmosis reduction device comprises:
a wrap of elastic material extending a length L from a first end to a second end with a width, the wrap having an open window or slot positioned in an intermediate portion of the wrap spaced from the first and the second ends, the open window or slot being reinforced thicker around a perimeter relative to the wrap, and wherein the improved syndesmosis reduction device requires no clamps or fasteners when used, wherein the wrap is in a rectangular shape extending a length L of 7 feet to 10 feet from a first end to a second end with a width W of 9 inches, the wrap having a 2 to 4 inch wide seamed or reinforced window or slot having a length of 2 to 4 feet and a width positioned in an intermediate portion of the wrap spaced from the first and the second ends, the open window or slot being reinforced thicker around a perimeter of the window relative to the wrap, and wherein the wrap is configured to be used to reduce a syndesmotic injury by wrapping the wrap to better direct reduction vector forces on a fibula without a clamp, wherein the wrap is configured to allow a reduction to be facilitated when using the wrap by circumferentially wrapping the wrap from a leg to a foot or vice versa in a compressive fashion by securing the first end by wrapping and stretching the wrap to the second end in the absence of clamps and wherein the wrap is made of any elastic rubber or elastic polymers, elastic woven fabrics, or other stretchable materials and only reinforced along the perimeter of the window.

* * * * *